US006928354B2

United States Patent
Ryu et al.

(10) Patent No.: US 6,928,354 B2
(45) Date of Patent: Aug. 9, 2005

(54) APPARATUS AND METHOD FOR CONTROLLING VEHICLE BRAKE USING BRAIN WAVES

(75) Inventors: Chang Su Ryu, Daejon-Shi (KR); Yoon Seon Song, Daejon-Shi (KR); Seung Hoon Nam, Daejon-Shi (KR); Tae Gyu Yim, Daejon-Shi (KR)

(73) Assignee: Electronics and Telecommunications Research Institute (KR)

(*) Notice: Subject to any disclaimer, the term of this patent is extended or adjusted under 35 U.S.C. 154(b) by 0 days.

(21) Appl. No.: 10/671,267

(22) Filed: Sep. 24, 2003

(65) Prior Publication Data

US 2004/0117098 A1 Jun. 17, 2004

(30) Foreign Application Priority Data

Dec. 12, 2002 (KR) ................................. 10-2002-0079288

(51) Int. Cl.[7] .............................. B80T 8/00; G06F 19/00
(52) U.S. Cl. ............................ 701/70; 701/36; 188/2 R; 280/28.11
(58) Field of Search ................................ 701/70, 1, 36; 303/1, 2, 13; 188/2 R, 382; 280/28.11

(56) References Cited

U.S. PATENT DOCUMENTS

| | | | |
|---|---|---|---|
| 5,321,407 A | * 6/1994 | Kikuchi et al. | ............... 342/70 |
| 5,473,538 A | * 12/1995 | Fujita et al. | ................... 701/45 |
| 5,492,394 A | * 2/1996 | Kusano et al. | ........... 303/113.2 |
| 5,638,826 A | 6/1997 | Wolpaw et al. | |
| 5,840,040 A | 11/1998 | Altschuler et al. | |
| 6,175,762 B1 | 1/2001 | Kirkup et al. | |
| 6,254,536 B1 | 7/2001 | DeVito | |
| 6,351,698 B1 | * 2/2002 | Kubota et al. | ................ 701/51 |

OTHER PUBLICATIONS

English abstrac of JPO02001030886–Hirano–Feb. 6, 2001—Braking device based on brain waves.*

* cited by examiner

*Primary Examiner*—Olga Hernandez
(74) *Attorney, Agent, or Firm*—Blakely Sokoloff Taylor & Zafman

(57) ABSTRACT

Disclosed are an apparatus and method for controlling vehicle brake using the brain waves. A driver controls the brake using the characteristic of the brain waves appearing before the driver's movement in the course of stepping on the brake pedal for braking in a dangerous condition. Therefore, the brake can be operated faster, and a condition where the brake is operated in an unwanted situation is prevented to prevent a traffic accident in advance. Further, the present invention does not require a driver's specific intentional behavior or psychological action except for natural behavior for braking (behavior to step on the brake pedal). Accordingly, the present invention makes a user convenient and is suitable for an ordinary person.

10 Claims, 2 Drawing Sheets

APPARATUS AND METHOD FOR CONTROLLING VEHICLE BRAKE USING BRAIN WAVES

BACKGROUND OF THE INVENTION

1. Field of the Invention

The present invention relates to apparatus and method for controlling vehicle break using brain waves, and more particularly, to apparatus and method for controlling vehicle break using brain waves, capable of operating the brake faster using a characteristic of the brain waves appearing before a driver steps on the brake pedal.

2. Background of the Related Art

In recent years, in order to provide users with more convenient interface, an attempt has been made on development of a user-friendly interface using voice, a facial expression, gesture and bio-signal [brain waves, electrooculogram, electromyogram, etc.].

In case of the brain waves being a representative bio-signal, they are used for learning or meditation by applying a bio-feedback mode to an alpha rhythm appearing in the eye-closed and stable state. A technology for moving a cursor on the monitor and controlling the electronic devices, using a specific brain wave, has been developed.

U.S. Pat. No. 6,254,536 entitled "Method & apparatus for measuring & analyzing physiological signals for active or passive control of physical & virtual spaces & the contents therein" issued to D. DeVito, discloses the apparatus and method for controlling the electronic devices using variation in the bio-signal due to face's wrinkle, abrupt movement of one's gaze or induction of emotion. The above patent, however, has a disadvantage that a user's intention (e.g. to switch on) to control the electronic devices by doing the specific behavior and a measure (e.g. face's wrinkle) for realizing the user's intention are not naturally connected.

Meanwhile, U.S. Pat. No. 5,840,040 (entitled "Encephalolexianalyzer") issued to E. L. Altschuler and F. U. Dowla discloses a technology in which communication is established using a mu rhythm that is varied when movement is imagined or performed, like Morse code. U.S. Pat. No. 6,175,762 (entitled "EEG based activation system") issued to L. Kirkup, etc. discloses a technology in which the switch is turned on/off using an alpha rhythm amplified when the eyes are closed. However, these prior arts have a problem that they cause a user's inconvenience since they requires the user to take specific intentional behavior (i.e., to close the eyes for the purpose of turning on the switch, etc.) in order to realize his or her intention.

Another prior art, U.S. Pat. No. 5,638,826 (entitled "Communication method and system using brain waves for multidimensional control") issued to J. R. Wolpaw and D. J. McFarland discloses a technology in which the handicapped moves the cursor on the monitor using the mu rhythm that is varied when the handicapped imagines movement. However, this patent has problems that it requires lost of time for a user's exercise and is not suitable for ordinary persons.

Meanwhile, still another prior arts for controlling the vehicle brake using the brain waves include Korean Patent Application Nos. 1993-21335 (entitled "Apparatus for automatically controlling the brake using the brain waves and method thereof") and 1996-57464 (entitled "Brake control apparatus through sensing of the brain waves by the driver"). These patents, however, employ a method of recognizing the brain waves appearing in emergency to control the brake. Behavior that may be taken by the driver in emergency (dangerous condition) may include acceleration (i.e., behavior taken to prevent rear-end collision by a vehicle coming from the rear), deceleration (i.e., behavior taken to prevent collision with a vehicle or a walker), and a change of direction through manipulation of the vehicle handle (i.e., when a vehicle suddenly cuts in from the side line). As in the prior arts, if the brake is operated in any case of emergency, there is a high possibility that a traffic accident may happen. Further, even in case where the brake is operated after a dangerous condition is recognized on a snowy or rainy road, driving conditions may be further deteriorated (i.e., sliding or rotation on the snowy or rainy road). Therefore, there is a problem that operating the brake only by recognition of the dangerous condition through the brain waves is accompanied by lots of danger.

SUMMARY OF THE INVENTION

Accordingly, the present invention has been made in view of the above problems, and it is an object of the present invention to provide an apparatus and method for controlling vehicle brake using brain waves, which are convenient to users and suitable for ordinary persons, in such a manner that it does not operate the brake in unwanted situation while faster operating the brake in wanted situation, by allowing a driver to control the brake using a characteristic of the brain waves appearing before a driver's movement is made in the course of stepping on the brake pedal in order to avoid a dangerous condition, and that it does not require specific intentional behavior or psychological action except for the driver's natural behavior (behavior taken to step on the brake pedal) for controlling the vehicle.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve the above objects, according to the present invention, there is provided an apparatus for controlling a vehicle brake using brain waves, including a brain wave detector for detecting a central beta rhythm of a driver's brain waves appearing before the driver's movement to step on the brake pedal after the step of determining driving conditions, a brain wave amplifier for amplifying the brain waves detected by the brain wave detector, an A/D converter for converting the brain waves amplified by the brain wave amplifier into a digital data, and a controller for sensing the driver's movement for braking by analyzing the brain waves converted into the digital data in the A/D converter and then generating a command for braking the vehicle.

In another aspect of the present invention, there is provided a method for controlling a vehicle brake using brain waves, including a step of determining driving conditions, a detection step of detecting a central beta rhythm of a driver's brain waves appearing before the driver's movement to step on a brake pedal, an amplification step of amplifying the central beta rhythm detected in the detection step, an A/D conversion step of converting the amplified central beta rhythm into a digital data, and a control step of sensing the driver's movement for braking by comparing the central beta rhythm that was converted into the digital data in the A/D conversion step with a reference brain wave and then generating a command for braking the vehicle.

In another aspect of the present invention, it is to be understood that both the foregoing general description and the following detailed description of the present invention are exemplary and explanatory and are intended to provide further explanation of the invention as claimed.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

The present invention is related to an apparatus and method for controlling vehicle brake using brain waves, capable of operating the vehicle brake faster using a characteristic of the brain waves appearing before a driver's movement in the course of stepping on the brake pedal.

Reference will now be made in detail to the preferred embodiments of the present invention, examples of which are illustrated in the accompanying drawings.

Figure 1:
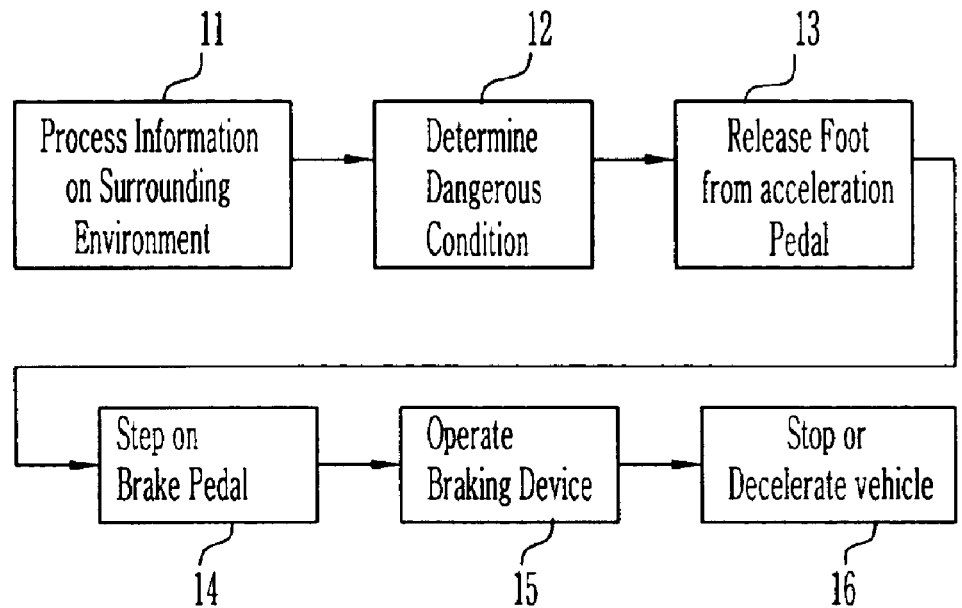
FIG. 1 is a flowchart illustrating a process from when a driver steps on a vehicle's brake pedal in a dangerous condition to when the vehicle is stopped.

FIG. 1 is a flowchart illustrating a process from when a driver steps on a vehicle's brake pedal in a danger condition to when the vehicle is stopped. A driver processes information (usually visual information) on driving conditions (step 11) and determines whether a dangerous condition exist (step 12). If the driver determines that there is the dangerous condition, the driver releases his or her foot from the acceleration pedal (step 13) and then steps on the brake pedal (step 14). Next, a braking device is operated (step 15) and the vehicle is decelerated and stopped (step 16).

In the prior art, the vehicle brake is controlled using variation in the brain waves depending on the driver's psychological state that varies in the step 12 for determining the dangerous condition. In the present invention, however, a driver's intention for braking is determined using the characteristic of the brain waves related to movement appearing before the brake pedal is stepped on in the steps 13 and 14 wherein the driver tries to step on the brake pedal after the dangerous condition.

As described above, movement that may be taken by the driver in the dangerous condition may include deceleration, acceleration, a change of direction, etc. It is difficult to determine in detail whether a specific situation is a situation requiring deceleration, a situation requiring acceleration or a situation requiring the change of direction, using the brain waves, in the step 12 for determining the dangerous condition. For this reason, the method to determine a driver's intention for braking in the present invention is for preventing a malfunction that may happen when the brake is operated only through the determination of the dangerous condition and a danger that may be caused accordingly. Therefore, in the present invention, the brake device is operated before the driver's actual movement occurs (before the driver steps on the brake pedal), using the characteristic of the brain waves appearing before the driver performs movement for deceleration or braking in the steps 13 and 14 after the step 12 for determining the dangerous condition.

For example, in case of a vehicle that is driven at the rate of 60 Km/hour, it can be said that the vehicle is driven at the rate of about 16.7 m/second. According to the experiment made in the field of cognitive science, approximately 300 ms is taken for the driver to move his or her fingers to a neighboring button in a situation where the button is pressed with the fingers. It is assumed that 300 ms is taken for the driver to move his or her foot from the acceleration pedal to the brake pedal. Then, it was found that the vehicle is moved by about 5 m during the interval. This means the time interval required to corresponding movement after determination at the brain. This could not be shortened by improving the braking system. Further, considering that the foot's movement is slower than the hand's movement, this distance may be further lengthened. Therefore, in the present invention, the brake is operated before 300 ms or earlier, which is taken to step on the brake pedal, using the characteristic of the brain waves appearing before the brake pedal is stepped on. It is thus possible to shorten the above distance (5 m at the rate of 60 Km/hour). Meanwhile, the characteristic of the brain waves appearing in the concrete operating step, not the step of determining the dangerous condition (step 12), i.e., when movement for stepping on the brake pedal is performed (acceleration pedal is released and the brake pedal is then to be stepped on) is employed. It is thus possible to prevent a malfunction and reduce a traffic accident, without additional intentional psychological action or behavior except for movement to step on the brake pedal.

Many researches have been made on brain-wave components relating to movement [see G. Pfurtscheller and F. H. Lopes da Silva, "Event-related EEG/MEG synchronization and desynchronization": basic principles, Clin. Neurophisiol. 110, 1842–1857 (1999)]. It is known that the mu rhythm and the beta rhythm that were measured in the central region of the scalp corresponding to the motor area of the brain decrease before movement starts and increase after movement starts, which thus result in returning to their original states. Further, mu rhythm and beta rhythm related to movement could be sensed over a wide range covering the central region, the parietal region and the frontal region of the scalp. Thus, there is an advantage that a brain wave detector of a headphone-type (electrode for measuring the brain waves is located within the head support of the common headphone) can be used.

The present invention does not require a driver's specific intentional behavior or psychological action except for natural behavior for braking (behavior for stepping on the brake pedal). The prevent invention can give a user convenience by allowing the user to mount the brain wave detector of the common headphone-type thereon.

Figure 2:
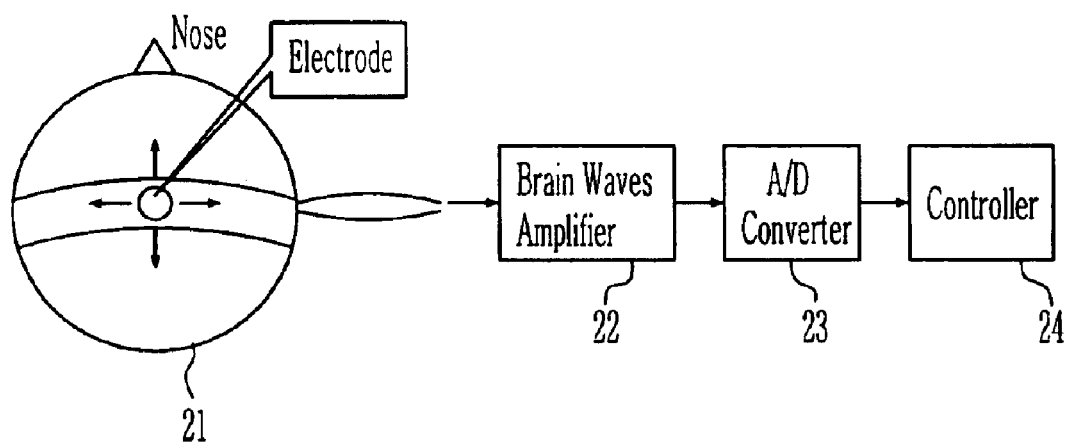
FIG. 2 is a block diagram illustrating the operational process of an apparatus for controlling vehicle brake using brain waves according to one embodiment of the present invention.

FIG. 2 is a block diagram illustrating the operational process of the apparatus for controlling vehicle brake using brain waves according to one embodiment of the present invention.

The brain waves are detected by a brain wave detector 21 having a headphone-type. FIG. 2 shows the brain wave detector 21 viewed from the top. An electrode can be moved right and left within the support of the headphone. A reference electrode that is usually attached to an earlobe may be inserted into the earcup of the headphone. Position of the electrode for detecting the brain waves within the support of the headphone may be usually Cz, Pz or Fz of 10-20 international nomenclature (International 10-20 System of Electrode Placement), or may be adjusted depending on the user.

The signals detected in the brain wave detector 21 are amplified in an amplifier 22. At this time, the amplifier 22 performs filtering for 60 Hz AC current that is usually performed when the brain waves are measured. The amplified brain waves are then converted into a digital data by means of an A/D converter 23. Next, a controller 24 recognizes a characteristic of the brain waves appearing before a driver starts movement using the method provided by the present invention and then generates a command for operating the brake device.

Figure 3:
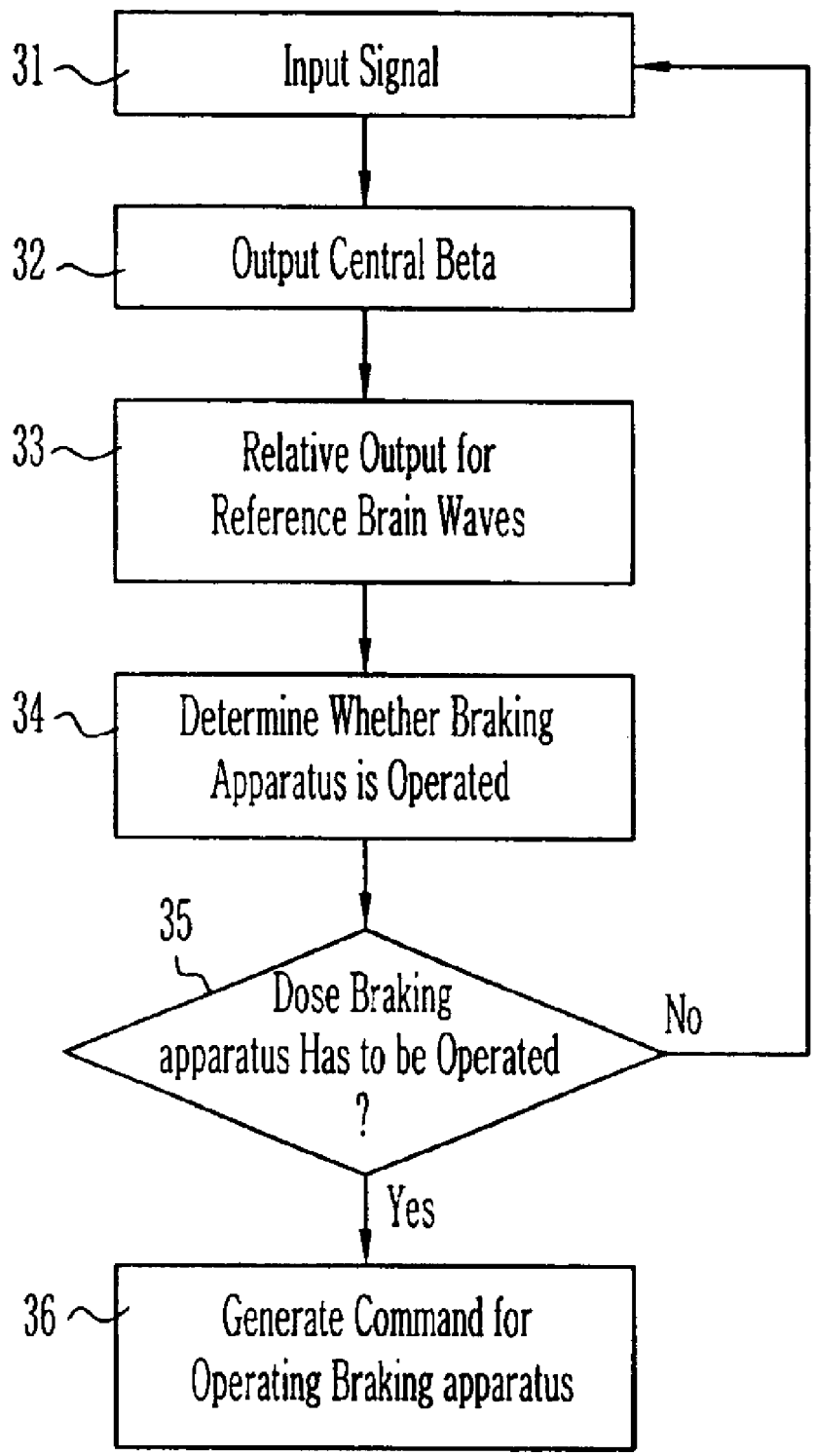
FIG. 3 is a flowchart illustrating the operational process of a controller used for the apparatus for controlling vehicle brake using brain waves according to the present invention.

FIG. 3 is a flowchart illustrating the operational process of a controller used for the apparatus for controlling vehicle brake using brain waves according to the present invention. This process includes five steps.

The brain wave signal is inputted from the A/D converter 23 in FIG. 2 (step 31). The power of a specific frequency region for the brain wave signal in a predetermined time period is then obtained (step 32). For example, the time period may be 0.25~0.5 second and may be overlapped. In the present invention, the beta rhythm of 18–26 Hz (hereinafter called "central beta", which was obtained from the central region, the parietal region or the frontal region of the scalp) is used as the specific frequency region. The mu rhythm of 10–12 Hz in frequency, of the brain waves that were widely used in the prior art, may be contaminated due to slow waves caused by eye blink, respiration, or the like. In the brake control apparatus of the present invention, therefore, the central beta is used instead of the mu rhythm. The region of the central beta may be a little changed depending on the user.

The power of the central beta in a predetermined time period may be obtained using FFT (fast Fourier transform). Also, the power may be obtained by squaring the amplitude of the signal obtained from the band pass filter and averaging over the time period. It should be noted that the present invention could be applied to a method that is usually used by those skilled in the art.

A brain wave of baseline (rest state with no movement) is used as the reference brain wave. The power of the central beta for the brain wave measured for baseline is obtained and is stored on the storage device. The power of the central beta of the reference brain wave may be changed at any time by the driver in order to efficiently use the vehicle brake control apparatus using brain waves. A relative power (step 33) to the reference brain wave is obtained by dividing the power (step 32) of the central beta obtained in the above by the power of the central beta of the reference brain wave.

It is determined that the braking device has to be operated (step 34) by checking the relative power (step 33) and a pressed state of the acceleration pedal. As the result of the determination, if the acceleration pedal is not pressed and the relative power (step 33) is lower than a predetermined threshold, the operation of the braking device is set to generate an operation command. If not, the signal is continuously inputted from the A/D converter.

In the above, whether the braking device has to be operated or not may be decided using an artificial neural network with the relative output at each frequency of the central beta rhythm as an input, instead of determining whether the braking device has to be operated by comparing the output with a predetermined threshold.

An area governing behaviors of the foot in the motor region of the brains corresponds to the vertex of the head. It is thus difficult to discriminate the left side and the right side (i.e., left foot, right foot) since the region is narrow. Accordingly, it is difficult to discern a situation wherein the foot is released from the acceleration pedal for transmission and the foot steps on the clutch, not the brake pedal. The present invention can be applied to an automatic transmission vehicle not a manual transmission vehicle.

As described above, in the vehicle brake control apparatus and method using the brain waves according to the present invention, a driver controls the brake using the characteristic of the brain waves appearing before his or her movement in the course of stepping on the brake pedal for braking in a dangerous condition. Therefore, the present invention has new effects that it can operate the brake faster and prevent a condition where the brake is operated in an unwanted situation to avoid a traffic accident in advance. Further, the present invention has advantageous effects that it does not require a driver's specific intentional behavior or psychological action except for natural behavior for braking (movement to step on the brake pedal) and it makes a user convenient by allowing the user to mount a brain wave detector of a headphone type thereon.

The forgoing embodiments are merely exemplary and are not to be construed as limiting the present invention. The present teachings can be readily applied to other types of apparatuses. The description of the present invention is intended to be illustrative, and not to limit the scope of the claims. Many alternatives, modifications, and variations will be apparent to those skilled in the art.

What is claimed are:

1. An apparatus for controlling vehicle brake using brain waves, comprising:
    a brain wave detector for detecting a central beta rhythm of 18–26 Hz obtained from one of a central region, a parietal region and a frontal region of a scalp of a driver's brain waves appearing before the driver's movement to step on a brake pedal after determining driving conditions;
    a brain wave amplifier for amplifying the brain waves detected by the brain wave detector;
    an A/D converter for converting the brain waves amplified by the brain wave amplifier into a digital data; and
    a controller for sensing the driver's movement for braking by analyzing the brain waves converted into the digital data in the AID converter and then generating a command for braking the vehicle,
wherein the central beta rhythm of 18–26 Hz is a range not contaminated due to an eye blink.

2. The apparatus of claim 1, wherein the central beta rhythm of 18–26 Hz is a range not contaminated due to respiration.

3. The apparatus as claimed in claim 1, wherein the brain wave detector has a headphone-type shape in which an electrode is attached to a central region of the driver's scalp.

4. The apparatus as claimed in claim 3, wherein the electrode is one in number and is positioned in Cz, Pz or Fz of International 10-20 System of Electrode Placement.

5. A method for controlling vehicle brake using brain waves, comprising:
    detecting a central beta rhythm of 18–26 Hz obtained from one of a central region, a parietal region, and a frontal region of a scalp of a driver's brain waves appearing before the driver's movement to step on a brake pedal after determining driving conditions;
    amplifying the central beta rhythm;
    A/D converting the amplified central beta rhythm from analog data into a digital data; and controlling a vehicle brake, the controlling including:
    sensing the driver's movement for braking by comparing the central beta rhythm that was converted into the digital data in the A/D converting with a reference brain wave, and
    generating a command for braking the vehicle,
wherein the central beta rhythm of 18–26 Hz is a range not contaminated due to an eye blink.

6. The method as claimed in claim 5, wherein comparing includes determining that there exists movement for braking, if a relative power to the reference brain waves of the detected central beta rhythm is lower than a predetermined threshold, and then generating the vehicle braking command.

7. The method as claimed in claim 5, wherein the controlling includes operating the vehicle brake, by determining whether or not there is movement for braking by using an artificial neural network with the relative power at each frequency of the detected central beta rhythm as an input.

8. The method of claim 5, wherein the central beta rhythm of 18–26 Hz is a range not contaminated due to respiration.

9. The method of claim 5, wherein the central beta rhythm range of 18–26 Hz is a range not contaminated due to respiration.

10. An apparatus for controlling vehicle brake using brain waves, comprising:
    a brain wave detector for detecting a central beta rhythm of 18–26 Hz obtained from one of a central region, a parietal region and a frontal region of a scalp of a driver's brain waves appearing before the driver's movement to step on a brake pedal after determining driving conditions;
    a brain wave amplifier for amplifying the brain waves detected by the brain wave detector;
    an A/D converter for converting the brain waves amplified by the brain wave amplifier into a digital data; and
    a controller for sensing the driver's movement for braking by analyzing the brain waves converted into the digital data in the A/D converter and then generating a command for braking the vehicle,
wherein the controlling includes operating the vehicle brake, by determining whether or not there is movement for braking by using an artificial neural network with the relative power at each frequency of the detected central beta rhythm as an input is not contaminated due to eye blink.

* * * * *